US00PP19031P2

(12) United States Plant Patent
Talmadge

(10) Patent No.: US PP19,031 P2
(45) Date of Patent: Jul. 15, 2008

(54) ***SUTERA* PLANT NAMED 'BALABOLAV'**

(50) Latin Name: *Sutera grandiflora*
Varietal Denomination: Balabolav

(75) Inventor: Paul A. Talmadge, Orcutt, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/823,219

(22) Filed: Jun. 27, 2007

(51) Int. Cl.
*A01H 5/00* (2006.01)

(52) U.S. Cl. ..... Plt./485
(58) Field of Classification Search ..... Plt./485
See application file for complete search history.

(56) References Cited

U.S. PATENT DOCUMENTS

PP14,481 P3 * 1/2004 Westhoff ..... Plt./485
PP17,234 P3 * 11/2006 Stemkens ..... Plt./485

OTHER PUBLICATIONS

Canada Plant Breeders' Rights application No. 07–5880 filed Apr. 12, 2007—not published when this IDS was prepared.

* cited by examiner

*Primary Examiner*—Wendy C. Haas
(74) *Attorney, Agent, or Firm*—Audrey Charles

(57) ABSTRACT

A new and distinct cultivar of *Sutera* plant named 'Balabolav', characterized by its single type light lavender-colored flowers, dark green-colored foliage, and moderately vigorous, spreading and trailing growth habit.

1 Drawing Sheet

Latin name of genus and species of plant claimed: *Sutera grandiflora.*
Variety denomination: 'Balabolav'.

BACKGROUND OF THE INVENTION

The present invention relates to a new and distinct cultivar of *Sutera* plant botanically known as *Sutera grandiflora* and hereinafter referred to by the cultivar name 'Balabolav'.

The new cultivar originated in a controlled breeding program in Guadalupe, Calif. during June 2004. The objective of the breeding program was the development of *Sutera* cultivars that continuously flower with attractive flower coloration, dark green-colored foliage, excellent basal branching, and spreading growth habit.

The new *Sutera* cultivar is the result of open-pollination. The female (seed) parent of the new cultivar is the proprietary *Sutera grandiflora* breeding selection designated 5370-2, not patented, characterized by its blush white-colored flowers, dark green-colored foliage, and semi-upright and trailing growth habit. The male (pollen) parent of the new cultivar is unknown. The new cultivar was discovered and selected as a single flowering plant within the progeny of the above stated open-pollination during August 2005 in a controlled environment at Guadalupe, Calif.

Asexual reproduction of the new cultivar by terminal stem cuttings since August 2005 at Guadalupe, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balabolav' as a new and distinct cultivar of *Sutera* plant:

1. Single type, light lavender-colored flowers;
2. Dark green-colored foliage; and
3. Moderately vigorous, spreading and trailing growth habit.

Plants of the new cultivar differ from plants of the female parent primarily in flower color, flower size, and vigor.

Of the many commercially available *Sutera* cultivars, the most similar in comparison to the new cultivar is Scopia™ Gulliver Lilac, not patented. However, in side by side comparisons, plants of the new cultivar differ from plants of Gulliver Lilac in the following characteristics:

1. Plants of the new cultivar have smaller diameter flowers than plants of Gulliver Lilac;
2. Plants of the new cultivar have shorter corolla tubes than plants of Gulliver Lilac; and
3. Plants of the new cultivar have a flower color slightly different from plants of Gulliver Lilac.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balabolav'. The plants were grown in 4.5 inch pots for 9 weeks in a greenhouse at West Chicago, Ill.

DETAILED BOTANICAL DESCRIPTION

Figure 1:
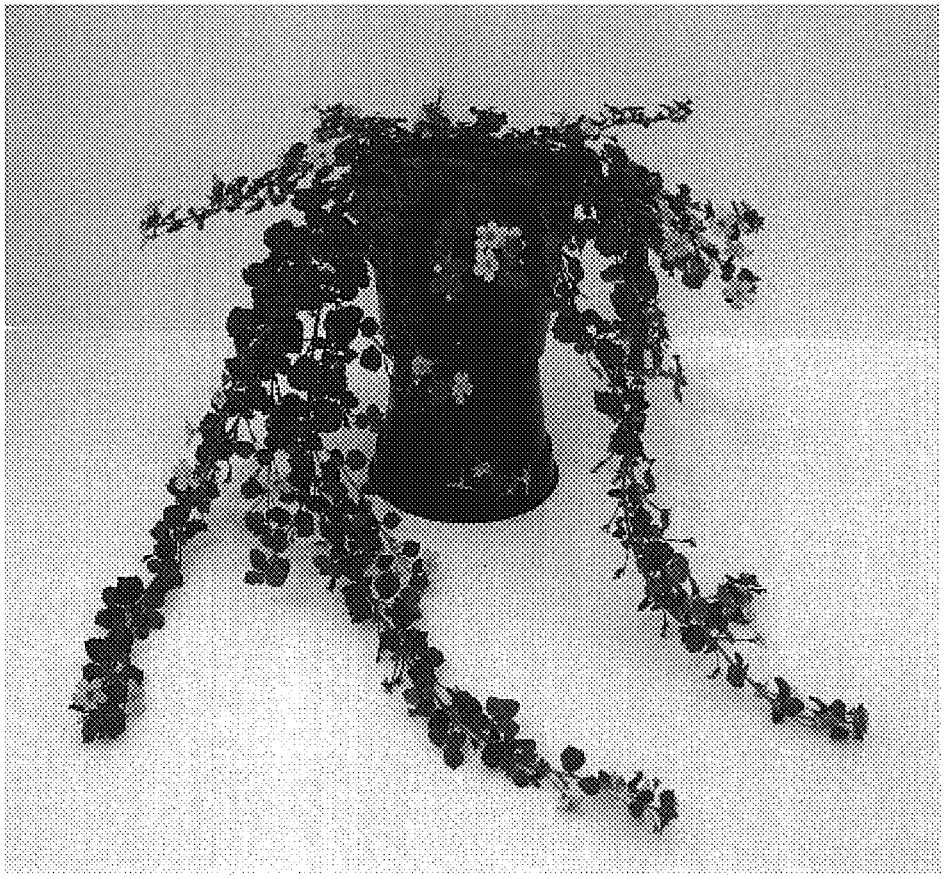
FIG. 1 illustrates a side view of the overall growth and flowering habit of 'Balabolav'.
Figure 2:
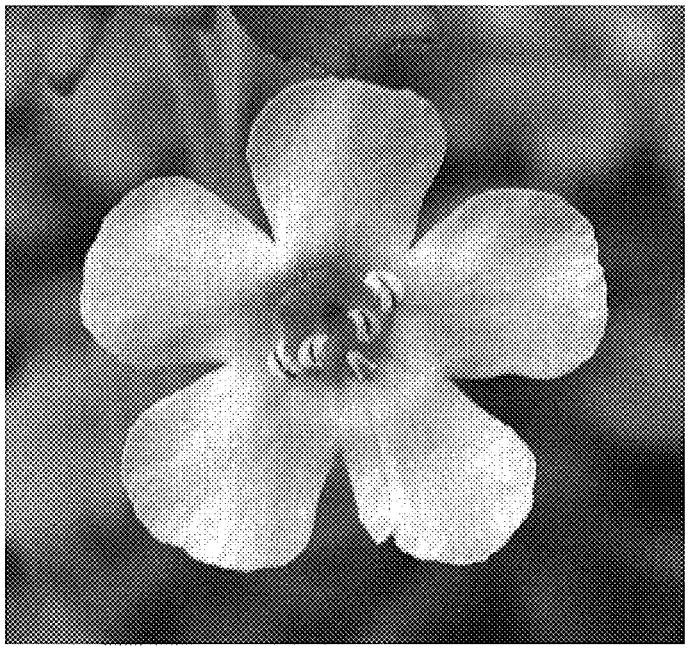
FIG. 2 illustrates a close-up view of an individual flower of 'Balabolav'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Apr. 9, 2007 between 9:00 a.m. and 10:00 a.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 9 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Sutera grandiflora* cultivar Balabolav.

Parentage:

*Female parent.*—Proprietary *Sutera grandiflora* breeding selection designated 5370-2, not patented.

*Male parent.*—Unknown.

Propagation:

*Type cutting.*—Terminal stem.

*Time to initiate roots.*—Approximately 10 to 13 days.

*Time to produce a rooted cutting.*—Approximately 21 to 24 days.

*Root description.*—Fibrous.

*Rooting habit.*—Freely branching.

Plant description:

*Commercial crop time.*—Approximately 5 to 7 weeks from a rooted cutting to finish in a 10 cm pot.

*Growth habit and general appearance.*—Moderately vigorous, spreading, trailing.

*Size.*—Height from soil level to top of plant plane: Approximately 4.4 cm. Width: Approximately 57.1 cm.

*Branching habit.*—Freely branching. Pinching will improve basal branching. Quantity of main branches per plant: Approximately 5.

*Branch.*—Strength: Strong. Length: Approximately 36.7 cm. Diameter: Approximately 2.0 mm. Length of central internode: Approximately 1.6 cm. Texture: Densely pubescent. Color of young and mature stems: 144A.

Foliage description:

*General description.*—Quantity of leaves per main branch: Approximately 41. Fragrance: None. Form: Simple. Arrangement: Opposite.

*Leaves.*—Aspect: Acute angle to stem; leaf blade transitions to an obtuse angle to stem with age. Shape: Broadly ovate. Margin: Serrate. Apex: Acute. Base: Attenuate. Venation pattern: Pinnate. Length of mature leaf: Approximately 1.8 cm. Width of mature leaf: Approximately 1.9 cm. Texture of upper and lower surfaces: Sparsely pubescent. Color of upper surface of young and mature foliage: 137A with indistinguishable venation. Color of lower surface of young and mature foliage: 137C with venation of 137D.

*Petiole.*—Length: Approximately 4.0 mm. Diameter: Approximately 1.0 mm. Texture: Sparsely pubescent. Color: 137D.

Flowering description:

*Flowering habit.*—'Balabolav' is freely flowering under outdoor growing conditions with substantially continuous blooming from spring through autumn and year-round in greenhouse environment.

*Lastingness of individual flower on the plant.*—Approximately 6 to 9 days.

Flower description:

*General description.*—Type: Solitary, axillary, salverform, and persistent. Quantity per plant: Approximately 37. Fragrance: None.

*Bud.*—Rate of opening: Generally takes 1 to 2 days for bud to progress from first color to fully open flower. Quantity per plant: Approximately 9.

*Bud just before opening.*—Shape: Obovoid. Length: Approximately 6.0 mm. Diameter: Approximately 3.0 mm. Texture: Densely glandular pubescent. Gland color: Colorless, transparent. Color: N155A.

*Corolla.*—Diameter: Approximately 1.5 cm.

*Petals.*—Quantity: 5, fused to form a tube. Shape: Obovate. Margin: Entire. Apex: Obtuse. Length from tube: Approximately 6.0 mm. Length of free portion: Approximately 5.0 mm. Width: Approximately 5.6 mm. Texture of upper and lower surfaces: Glabrous. Color of upper surface when first and fully open: 85B. Color of lower surface when first and fully open: 85C.

*Corolla tube.*—Length: Approximately 7.0 mm. Diameter at distal end: Approximately 3.0 mm. Diameter at proximal end: Approximately 1.0 mm. Texture of inner surface: Densely pubescent. Texture of outer surface: Densely glandular pubescent. Gland color: Colorless, transparent. Color of inner surface: 25A with throat of 13A. Color of outer surface: 191C with an overlay of 163at distal end.

*Peduncle.*—Strength: Strong. Aspect: Acute angle to stem. Length: Approximately 8.6 mm. Diameter: Less than 1 mm. Texture: Densely pubescent. Color: 144A.

*Sepals.*—Quantity per flower: 5, fused at base. Shape: Narrow linear. Apex: Acute. Length: Approximately 5.0 mm. Width: Approximately 1.0 mm. Texture of upper surface: Sparsely pubescent. Texture of lower surface: Densely pubescent. Color of upper surface: 137A. Color of lower surface: 144A at base transitioning to 137A toward apex.

*Reproductive organs.*—Androecium: Stamen quantity: 4 didynamous, basifixed. Stamen length of longer pair: Approximately 8.0 mm. Filament length of free portion of longer pair: Approximately 3.0 mm. Stamen length of shorter pair: Approximately 7.0 mm. Filament length of free portion of shorter pair: Approximately 2.0 mm. Filament color: Purer white than 155D. Anther shape: Funnel. Anther length: Less than 1 mm. Anther color: 16B with an overlay of 187A at opening. Pollen amount: Abundant. Pollen color: 16A. Gynoecium: Pistil quantity: 1 per flower. Pistil length: Approximately 9.3 mm. Stigma shape: Elongated, curved. Stigma length: Approximately 1.0 mm. Stigma color: 144B. Style length: Approximately 7.3 mm. Style color: 144D. Ovary length: Approximately 1.0 mm. Ovary color: 144A.

Seed and fruit production: Neither seed nor fruit production has been observed.

Disease and pest resistance: Resistance to pathogens and pests common to *Sutera* has not been observed.

What is claimed is:

1. A new and distinct cultivar of *Sutera* plant named 'Balabolav', substantially as herein shown and described.

* * * * *